(12) United States Patent
von Oepen (10) Patent No.: US 8,747,649 B2
(45) Date of Patent: Jun. 10, 2014

(54) ELECTROCHEMICAL FORMATION OF FOIL-SHAPED STENT STRUTS

(75) Inventor: Randolf von Oepen, Los Altos, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 271 days.

(21) Appl. No.: 13/107,216

(22) Filed: May 13, 2011

(65) Prior Publication Data
US 2012/0285836 A1 Nov. 15, 2012

(51) Int. Cl.
*C25F 3/16* (2006.01)
*C25F 7/02* (2006.01)
*A61F 2/82* (2013.01)

(52) U.S. Cl.
CPC ... *C25F 3/16* (2013.01); *C25F 7/02* (2013.01); *A61F 2/82* (2013.01)
USPC .............................. 205/668; 205/640; 205/670

(58) Field of Classification Search
CPC ................................................ A61F 2/82–2/97
USPC .................... 205/668; 623/1.1–1.54
See application file for complete search history.

(56) References Cited

U.S. PATENT DOCUMENTS

| | | | |
|---|---|---|---|
| 5,108,417 A | 4/1992 | Sawyer | |
| 5,344,425 A * | 9/1994 | Sawyer | 606/198 |
| 5,500,013 A | 3/1996 | Buscemi et al. | |
| 5,551,954 A | 9/1996 | Buscemi et al. | |
| 5,718,713 A | 2/1998 | Frantzen | |
| 5,746,691 A | 5/1998 | Frantzen | |
| 5,769,883 A | 6/1998 | Buscemi et al. | |
| 5,968,092 A | 10/1999 | Buscemi et al. | |
| 6,027,526 A | 2/2000 | Limon et al. | |
| 6,086,455 A | 7/2000 | Frantzen | |
| 6,183,353 B1 | 2/2001 | Frantzen | |
| 6,273,910 B1 | 8/2001 | Limon | |
| 6,273,911 B1 | 8/2001 | Cox et al. | |
| 6,375,826 B1 * | 4/2002 | Wang et al. | 205/684 |
| 6,387,124 B1 | 5/2002 | Buscemi et al. | |
| 6,514,284 B1 | 2/2003 | Cheng | |
| 6,537,202 B1 | 3/2003 | Frantzen | |
| 6,629,994 B2 | 10/2003 | Gomez et al. | |
| 6,652,576 B1 | 11/2003 | Stalker | |
| 6,679,980 B1 | 1/2004 | Andreacchi | |
| 6,869,443 B2 | 3/2005 | Buscemi et al. | |
| 6,899,729 B1 | 5/2005 | Cox et al. | |

(Continued)

FOREIGN PATENT DOCUMENTS

| | | |
|---|---|---|
| EP | 1369099 A | 12/2003 |
| WO | 0161080 A1 | 8/2001 |
| WO | WO 2010095664 A1 * | 8/2010 |

OTHER PUBLICATIONS

International Search Report dated Apr. 1, 2013.

*Primary Examiner* — James Lin
*Assistant Examiner* — Ho-Sung Chung
(74) *Attorney, Agent, or Firm* — Fulwider Patton LLP (57) ABSTRACT

An apparatus and method for electrochemically treating the struts of an intravascular stent is disclosed. An intravascular stent is mounted in a chamber and is electrochemically treated in order to remove a portion of the stent struts in order to form an airfoil shape. The airfoil-shaped stent struts will reduce turbulent blood flow in the vasculature in which the stent is implanted thereby improving clinical outcome.

4 Claims, 5 Drawing Sheets

(56) References Cited

U.S. PATENT DOCUMENTS

| | | |
|---|---|---|
| 6,979,346 B1 | 12/2005 | Hossainy et al. |
| 7,156,869 B1 | 1/2007 | Pacetti |
| 7,541,715 B2 | 6/2009 | Chiang et al. |
| 7,776,189 B2 | 8/2010 | Shrivastava et al. |
| 7,785,098 B1 | 8/2010 | Appleby et al. |
| 7,803,179 B2 | 9/2010 | Denison |
| 7,806,925 B2 | 10/2010 | Buscemi et al. |
| 7,823,263 B2 | 11/2010 | Wu |
| 7,893,413 B1 | 2/2011 | Appleby et al. |
| 2005/0098444 A1 | 5/2005 | Schaeffer |
| 2007/0286941 A1* | 12/2007 | Huang et al. ............... 427/2.24 |
| 2008/0142050 A1* | 6/2008 | Hashish et al. ............ 134/22.12 |
| 2009/0255827 A1* | 10/2009 | Andreacchi et al. .......... 205/640 |
| 2010/0016950 A1* | 1/2010 | Berglund et al. ............ 623/1.15 |
| 2011/0301691 A1* | 12/2011 | Kamikihara et al. ........ 623/1.15 |

* cited by examiner

ELECTROCHEMICAL FORMATION OF FOIL-SHAPED STENT STRUTS

BACKGROUND

The invention relates generally to providing an apparatus for electrochemical removal of metal on products made from metals. More particularly, the invention relates to an apparatus for the electrochemical treatment of medical devices made of titanium, stainless steel, tungsten, nickel-titanium, tantalum, cobalt-chromium-tungsten, cobalt-chromium, and the like to form a more hemodynamically compatible device.

While a wide range of products or devices can be made from the listed metal alloys for use with the present invention, medical devices are particularly suitable due to the biocompatible characteristics of these alloys. Thus, for example, implantable medical devices or devices that are used within the human body are particularly suitable and can be made from these alloys that have been electrochemically treated in accordance with the present invention. More particularly, and as described in more detail herein, intravascular stents can be made from the listed alloys that have been electrochemically treated according to the invention. Thus, while the description of prior art devices and of the invention herein refers mainly to intravascular stents, the invention is not so limited to medical products or intravascular stents.

Stents are generally metallic tube shaped intravascular devices which are placed within a blood vessel to structurally hold open the vessel. The device can be used to maintain the patency of a blood vessel immediately after intravascular treatments and can be used to reduce the likelihood of development of restenosis. Expandable stents are frequently used as they may travel in compressed form to the stenotic site generally either crimped onto an inflation balloon or compressed into a containment sheath in a known manner.

Metal stents can be formed in a variety of expandable configurations such as helically wound wire stents, wire mesh stents, weaved wire stents, metallic serpentine stents, or in the form of a chain of corrugated rings. Expandable stents, such as wire mesh, serpentine, and corrugated ring designs, for example, do not possess uniformly solid tubular walls. Although generally cylindrical in overall shape, the walls of such stents are perforated often in a framework design of wire-like elements or struts connected together or in a weave design of cross threaded wire.

Expandable stents formed from metal offer a number of advantages and are widely used. Metallic serpentine stents, for example, not only provide strength and rigidity once implanted they also are designed sufficiently compressible and flexible for traveling through the tortuous pathways of the vessel route prior to arrival at the stenotic site. Additionally, metallic stents may be radiopaque, thus easily visible by radiation illumination techniques such as x-ray film.

It is highly desirable for the surface of the stent to be extremely smooth so that it can be inserted easily and experience low-friction travel through the tortuous vessel pathway prior to implantation. A roughened outer surface may result in increased frictional obstruction during insertion and excess drag during travel to the stenotic site as well as damaging the endothelium lining of the vessel wall. A rough surface may cause frictional resistance to such an extent as to prevent travel to desired distal locations. A rough finish may also cause damage to the underlying inflation balloon. A less rough finish decreases thrombogenicity and increases corrosion resistance.

Stents have been formed from various metals including stainless steel, tantalum, titanium, tungsten, nickel-titanium which is commonly called Nitinol, and alloys formed with cobalt and chromium. Stainless steel has been extensively used to form stents and has often been the material of choice for stent construction. Stainless steel is corrosion resistant, strong, yet may be cut into very thin-walled stent patterns.

Cobalt-chromium alloy is a metal that has proven advantages when used in stent applications. Stents made from a cobalt-chromium alloy may be thinner and lighter in weight than stents made from other metallic materials, including stainless steel. Cobalt-chromium alloy is also a denser metal than stainless steel. Additionally, cobalt-chromium stents are nontranslucent to certain electromagnetic radiation waves, such as X-rays, and, relative to stainless steel stents, provide a higher degree of radiopacity, thus being easier to identify in the body under fluoroscopy.

Metal stents, however, suffer from a number of disadvantages. They often require processing to eliminate undesirable burrs, nicks, or sharp ends. Expandable metal stents are frequently formed by use of a laser to cut a framework design from a tube of metal. The tubular stent wall is formed into a lattice arrangement consisting of metal struts with gaps therebetween. Laser cutting, however, typically is at high temperature and often leaves debris and slag material attached to the stent. Such material, if left on a stent, would render the stent unacceptable for implantation. Treatment to remove the slag, burrs, and nicks is therefore required to provide a device suitable for use in a body lumen.

Descaling is a first treatment of the surface in preparation for further surface treatment such as electropolishing. Descaling may include, for example, scraping the stent with a diamond file, followed by dipping the stent in a hydrochloric acid or an HCl mixture, and thereafter cleaning the stent ultrasonically. A successfully descaled metal stent should be substantially slag-free in preparation for subsequent electropolishing Further finishing is often accomplished by the well known technique of electropolishing. Grinding, vibration, and tumbling techniques are often not suited to be employed on small detailed parts such as stents.

Electropolishing is an electrochemical process by which surface metal is dissolved. Sometimes referred to as "reverse plating," the electropolishing process actually removes metal from the surface desired to be smoothed. The metal stent is connected to a power supply (the anode) and is immersed in a liquid electrolytic solution along with a metal cathode connected to the negative terminal of the power supply. Current is applied and flows from the stent, causing it to become polarized. The applied current controls the rate at which the metal ions of the anodic stent are generally removed and diffused through the solution to the cathode.

The rate of the electrochemical reaction is proportional to the current density. The positioning and thickness of the cathode in relation to the stent is important to make available an even distribution of current to the desired portion of the stent sought to be smoothed. For example, some prior art devices have a cathode in the form of a flat plate or a triangular or single wire loop configuration, which may not yield a stent or other medical device with a smooth surface on all exposed surfaces. For example, the prior art devices do not always provide a stent having a smooth surface on the inner tubular wall of the stent where blood flow will pass.

What is needed is an apparatus and a process for treating a product or device made of a metal alloy to remove metal from the product to create a more streamlined shape to enhance hemodynamic flow. The present invention satisfies this need.

SUMMARY OF THE INVENTION

The invention is directed to an improved apparatus and method for the electrochemical treatment of an intravascular stent formed from a metal alloy. The invention is directed to an apparatus and method for electrochemically treating the struts of an intravascular stent in order to remove a portion of the stent struts to form an airfoil shape. More particularly, the cross-section of one more struts of the stent have a shape that resembles an airfoil or a hydrofoil which will reduce turbulent blood flow in the vasculature in which the stent is implanted, thereby improving clinical outcome. In one embodiment, an electrical fixture holds a stent within an electrolitic bath. Preferably, the stent is held stationary within the electrical fixture while an electrolyte is flowed through the inner lumen of the stent. The stent is energized by subjecting it to a direct voltage or by applying a voltage to the fixture that contacts the stent. These contacts can be made by leads that are in electrical communication with a power source. A cathode is positioned within the stent to create an electrical current directed toward the inner lumen and inner diameter of the stent. When the stent is energized with a different electrical potential than that of the cathode, the material of the stent will begin to dissolve into the electrolyte. The electrolyte is constantly flowing through the inner lumen of the stent and as the metallic material of the stent dissolves, it will be swept out of the stent inner lumen by the flow of electrolytic.

DETAILED DESCRIPTION OF THE PREFERRED EMBODIMENTS

The present invention stent improves on existing stents by providing a longitudinally flexible stent having a uniquely designed pattern and novel interconnecting members. In addition to providing longitudinal flexibility, the stent of the present invention also provides radial rigidity and a high degree of scaffolding of a vessel wall, such as a coronary artery. The design of the highly flexible interconnecting members and their placement relative to an adjacent U-shaped member provides for a tightly compressed stent onto a catheter while maintaining a high degree of flexibility during delivery.

Figure 1:
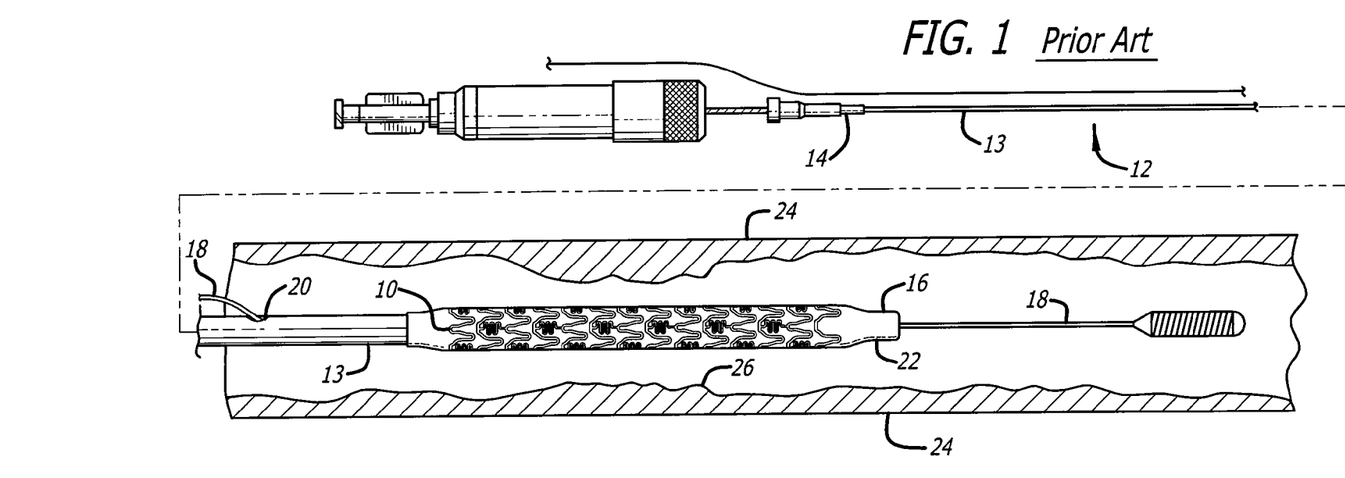
FIG. 1 an elevational view, partially in section, of a stent of the present invention mounted on a rapid exchange delivery catheter and positioned within an artery.

Turning to the drawings, FIG. 1 depicts a prior art stent 10 mounted on a conventional catheter assembly 12 which is used to deliver the stent and implant it in a body lumen, such as a coronary artery, peripheral artery, or other vessel or lumen within the body. The catheter assembly includes a catheter shaft 13 which has a proximal end 14 and a distal end 16. The catheter assembly is configured to advance through the patient's vascular system by advancing over a guide wire by any of the well known methods of an over the wire system (not shown) or a well known rapid exchange catheter system, such as the one shown in FIG. 1.

Catheter assembly 12 as depicted in FIG. 1 is of the well known rapid exchange type which includes an RX port 20 where the guide wire 18 will exit the catheter. The distal end of the guide wire 18 exits the catheter distal end 16 so that the catheter advances along the guide wire on a section of the catheter between the RX port 20 and the catheter distal end 16. As is known in the art, the guide wire lumen which receives the guide wire is sized for receiving various diameter guide wires to suit a particular application. The stent is mounted on the expandable member 22 (balloon) and is crimped tightly thereon so that the stent and expandable member present a low profile diameter for delivery through the arteries.

As shown in FIG. 1, a partial cross-section of an artery 24 is shown with a small amount of plaque that has been previously treated by an angioplasty or other repair procedure. Stent 10 is used to repair a diseased or damaged arterial wall which may include the plaque 26 as shown in FIG. 1, or a dissection, or a flap which are sometimes found in the coronary arteries, peripheral arteries and other vessels.

Figure 2:
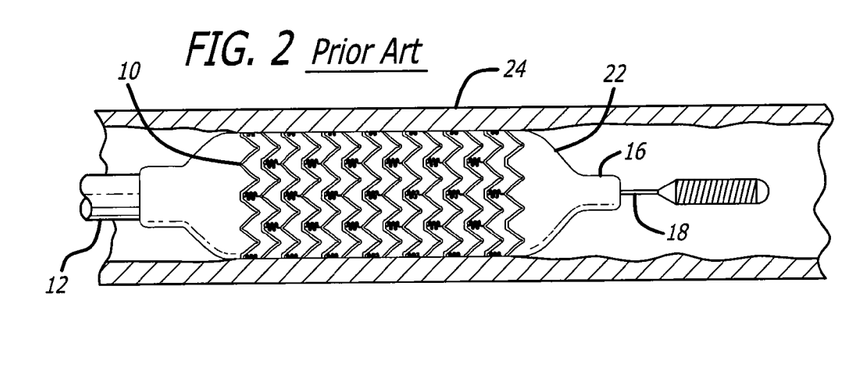
FIG. 2 is an elevational view, partially in section, similar to that in FIG. 1, wherein the stent is expanded within the artery, so that the stent embeds partially within the arterial wall.
Figure 3:
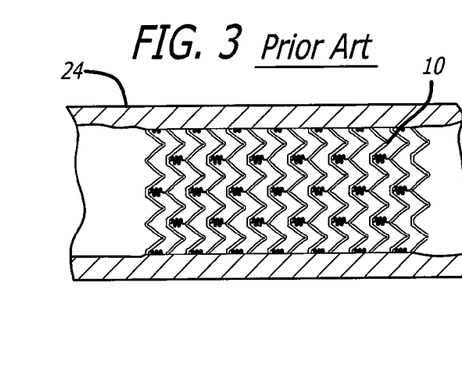
FIG. 3 is an elevational view, partially in section, showing the expanded stent implanted within the artery after withdrawal of the rapid exchange delivery catheter.

In a typical procedure to implant stent 10, the guide wire 18 is advanced through the patient's vascular system by well known methods so that the distal end of the guide wire is advanced past the plaque or diseased area 26. Prior to implanting the stent, the cardiologist may wish to perform an angioplasty procedure or other procedure (i.e., atherectomy) in order to open the vessel and remodel the diseased area. Thereafter, the stent delivery catheter assembly 12 is advanced over the guide wire so that the stent is positioned in the target area. The expandable member or balloon 22 is inflated by well known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIGS. 2 and 3, the balloon is fully inflated with the stent expanded and pressed against the vessel wall, and in FIG. 3, the implanted stent remains in the vessel after the balloon has been deflated and the catheter assembly and guide wire have been withdrawn from the patient.

The stent 10 serves to hold open the artery after the catheter is withdrawn, as illustrated by FIG. 3. Due to the formation of the stent from an elongated tubular member, the undulating components of the stent are relatively flat in transverse cross-section. When the stent is expanded, it is pressed into the wall of the artery, however, portions of the rectangular cross-section may protrude into the artery lumen and may interfere with the blood flow through the artery. The stent is pressed into the wall of the artery and will eventually be covered with endothelial cell growth which will minimize blood flow interference. The undulating portion of the stent provides good tacking characteristics to prevent stent movement within the artery. Furthermore, the closely spaced cylindrical elements at regular intervals provide uniform support for the wall of the artery.

Figure 4:
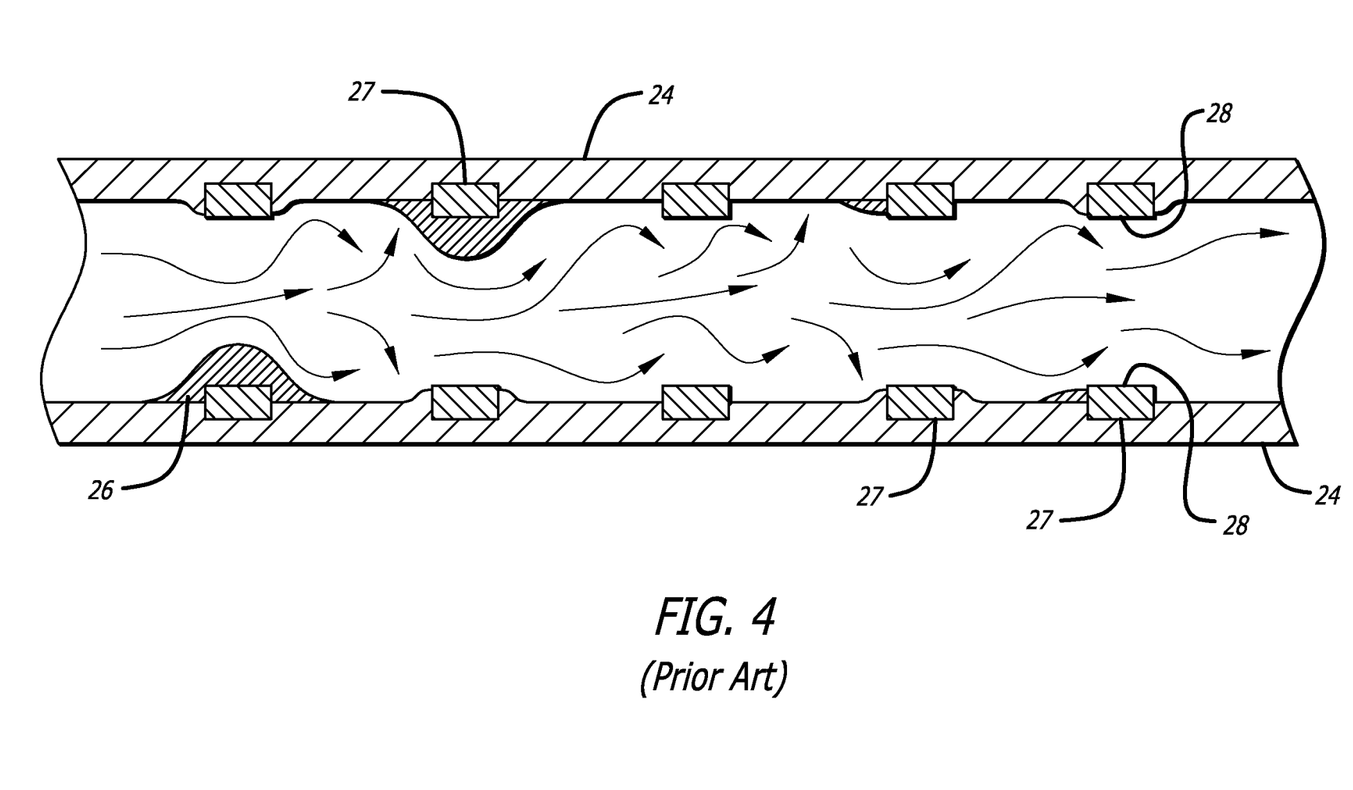
FIG. 4 is a cross-sectional view of a prior art stent in which the stent struts have a rectangular cross-section thereby causing turbulent flow of blood through the artery.

Referring to FIG. 4, a portion of an artery 24 is shown in cross-section with a typical prior art stent at least partially embedded in the artery wall. The stent is comprised of rectangular-shaped stent struts 27 that have an inner surface 28 that faces the blood flow. In FIG. 4, the blood is flowing from left to right in the artery. Because of the rectangular-shaped stent struts 27 having a vertical surface impeding blood flow, there is some turbulent blood flow in and around the stent struts as shown by the diagrammatic arrows in FIG. 4. These localized areas of turbulent blood flow produce adverse vascular reactions such as the proliferation of restenosis and the formation of plaque 26. Typically, the rectangular-shaped stent struts 27 will have rounded corners due to electropolishing, however, even though the corners have been rounded there is still turbulent blood flow that may produce the adverse vascular reactions.

Figure 5:
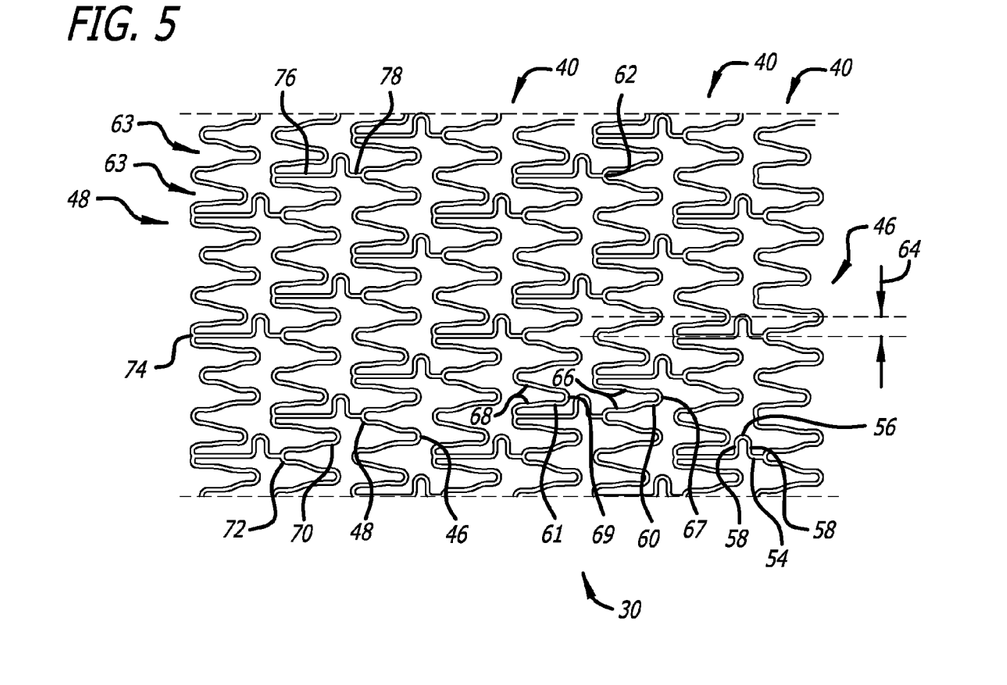
FIG. 5 is a plan view of a flattened stent of one embodiment of the invention which illustrates a pattern of rings and links.

Referring to FIG. 5, stent 30 is shown in a flattened condition so that the pattern can be clearly viewed, even though the stent is in a cylindrical form in use. The stent is typically formed from a tubular member.

Figure 6:
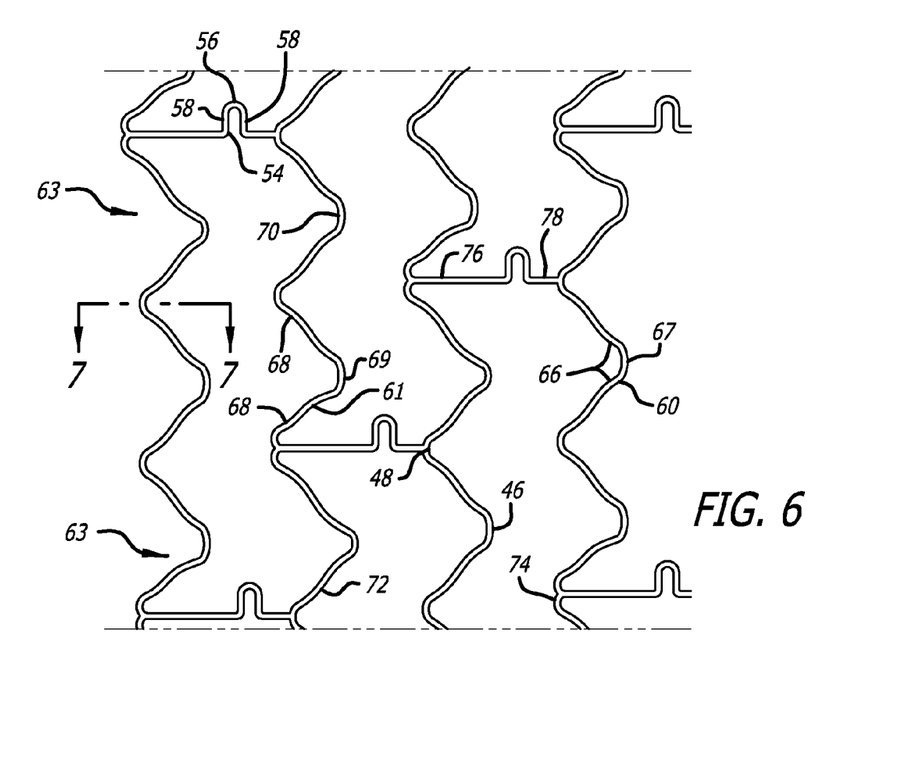
FIG. 6 is a partial plan view of the stent of FIG. 5 which has been expanded to approximately 4.0 mm inside diameter.

As shown in FIGS. 5-6, stent 30 is made up of a plurality of cylindrical rings 40 which extend circumferentially around the stent when it is in a tubular form (see FIG. 3). Each cylindrical ring 40 has a cylindrical ring proximal end 46 and a cylindrical ring distal end 48. Typically, since the stent is laser cut from a tube there are no discreet parts such as the described cylindrical rings and links. However, it is beneficial for identification and reference to various parts to refer to the cylindrical rings and links and other parts of the stent as follows.

Each cylindrical ring 40 defines a cylindrical plane 50 which is a plane defined by the proximal and distal ends 46,48 of the ring and the circumferential extent as the cylindrical ring travels around the cylinder. Each cylindrical ring includes cylindrical outer wall surface 52 which defines the outermost surface of the stent, and cylindrical inner wall surface 53 which defines the innermost surface of the stent. Cylindrical plane 50 follows the cylindrical outer wall surface.

An undulating link 54 is positioned within cylindrical plane 50. The undulating links connect one cylindrical ring 40 to an adjacent cylindrical ring 40 and contribute to the overall longitudinal flexibility to the stent due to their unique construction. The flexibility of the undulating links derives in part from curved portion 56 connected to straight portions 58 wherein the straight portions are substantially perpendicular to the longitudinal axis of the stent. Thus, as the stent is being delivered through a tortuous vessel, such as a coronary artery, the curved portions 56 and straight portions 58 of the undulating links will permit the stent to flex in the longitudinal direction which substantially enhances delivery of the stent to the target site. The number of bends and straight portions in a link can be increased or decreased from that shown, to achieve differing flexibility constructions. With the straight portions being substantially perpendicular to the stent longitudinal axis, the undulating link acts much like a hinge at the curved portion to provide flexibility. A straight link that is parallel to the stent axis typically is not flexible and does not add to the flexibility of the stent.

Referring to FIGS. 5-6, the stent 30 can be described more particularly as having a plurality of first peaks 60, second peaks 61, and valleys 62. Although the stent is not divided into separate elements, for ease of discussion references to peaks and valleys is appropriate. The number of peaks and valleys can vary in number for each ring depending upon the application. Thus, for example, if the stent is to be implanted in a coronary artery, a lesser number of peaks and valleys are required than if the stent is implanted in a peripheral artery, which has a larger diameter than a coronary artery. As can be seen for example in FIG. 6, peaks 60,61 are in phase 63, meaning that the peaks 60,61 point in the same direction and are substantially aligned along the longitudinal axis of the stent. It may be desirable under certain circumstances to position the peaks so that they are out of phase (not shown), that is, the peaks of one ring would be circumferentially offset from the peaks of an adjacent ring so that the apex of adjacent peaks pointed toward each other. As shown in FIGS. 5-6, the peaks are circumferentially offset 64 from the valleys and from the undulating link 54. Positioning the peaks, valleys, and undulating links in this manner, provides a stent having uniform expansion capabilities, high radial strength, a high degree of flexibility, and sufficient wall coverage to support the vessel.

Figure 7:
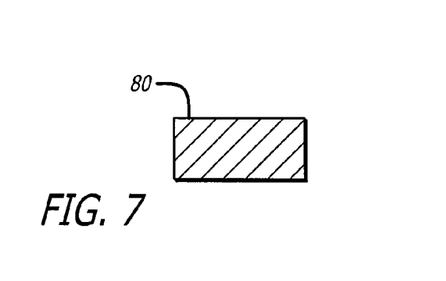
FIG. 7 is a cross-sectional view taken along lines 7-7 depicting a rectangular cross-section of a stent strut of FIG. 6.

As shown in FIG. 7, a rectangular-shaped stent strut 80 is shown in a transverse cross-sectional configuration from one of the peaks 69 from FIG. 6. More specifically, during a typical laser cutting of a thin metallic tube, the resulting transverse cross-sectional shape of all of the stent struts are generally a rectangular-shaped stent strut 80 like that shown in FIG. 7. Further processing including electropolishing will remove the sharp corners so that the basic overall rectangular shape remains, only with rounded corners so as to have a less invasive impact on the arterial wall when the stent is delivered and implanted. As previously described with respect to the rectangular-shaped stent struts in FIGS. 4 and 7, such a cross-sectional shape likely will result in turbulent blood flow and the adverse affects resulting therefrom. While FIG. 7 illustrates a rectangular-shaped stent strut, other cross-sectional configurations will benefit from the present invention as well. Thus, for example, a square cross-section, or any other cross-section having a leading edge that will disrupt blood flow, will benefit from the present invention.

As shown in FIGS. 8-10D, the stent of the present invention is placed in a chamber in which electrolytic solution flows through an inner lumen of the stent in order to remove metal from the stent struts and shape certain of the struts into an airfoil or hydrofoil shape. More specifically, those stent struts that are substantially perpendicular to the longitudinal axis of the stent and thereby the flow of the electrolytic solution, will be formed into a cross-sectional shape of a hydrofoil, in which the leading edge of the strut is thicker than the trailing end of the strut. When in use, as blood flows along the strut surface, it will maintain a laminar flow without disturbing the adjacent vasculature as much as if the stent strut were rectangular shaped thereby causing turbulent blood flow. While the stent struts of the present invention may not be a perfect airfoil shape or hydrofoil shape where the trailing edge would be relatively sharp, the trailing edge thickness is reduced compared to the leading edge thickness, but still has sufficient thickness to provide radial strength to hold the stent open and to avoid mechanically scoring or otherwise damaging the tissue of the vessel wall.

In keeping with the invention, as shown in FIGS. 8-11A, a chamber 82 has a longitudinal bore 84 extending therethrough and is configured for receiving a stent 30. The diameter of the longitudinal bore is configured to be slightly greater than the outer diameter of the stent 30 so that the stent 30 can be placed in the longitudinal bore without pushing on or having an interference fit that may damage the stent struts. The chamber 82 optionally has an end cap (not shown) that can be secured to the chamber by any conventional means such as screw threads (not shown) or a ratcheting lock, both of which are known in the art. A longitudinal axis 88 extends through the longitudinal bore 84 of the chamber. The chamber has a first end 90 and a second end 92 defining the overall length of the chamber, which can vary depending upon the length of the stent that is inserted therein.

Figure 8:
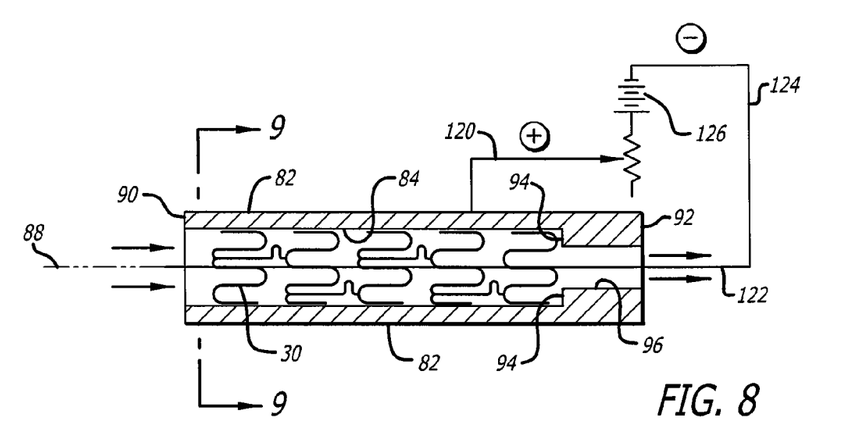
FIG. 8 is an elevational view, partially in section, of an assembly for pumping an electrolytic solution through the inner diameter of the stent to remove metal from the stent struts.

As shown in FIG. 8, the stent 30 is mounted or inserted into the longitudinal bore 84 and the outer diameter of the stent is just slightly less than the diameter of the longitudinal bore 84. In this embodiment, the stent 30 is held in place in the longitudinal bore by a flange or ridge 94 which will ensure that the stent does not move longitudinally as the electrolytic solution flows past the stent and removes metal. In this embodiment, a second longitudinal bore 96 is formed near the second end 92 of the chamber 82 wherein the second longitudinal bore has a diameter that is less than the outer diameter of the stent and less than the diameter of the longitudinal bore 84 in order to form the flange 94.

The longitudinal bore 84 has a diameter that is greater than the outer diameter of the stent 30. It is intended that different sized chamber 82 having different diameter longitudinal bores 84 be used for stents having different outer diameters. For example, a typical coronary artery stent in the manufactured configuration can have an outer diameter from between 2 mm to 3.5 mm, and have a length between 8 mm and 30 mm. More typically, a coronary stent has an outer diameter of about 3 mm and length of about 20 mm. The longitudinal bore 84 has a diameter that is greater than the outer diameter of the stent so that the stent can be easily inserted into the chamber 82 and into longitudinal bore 84 without scraping or damaging the stent struts. After the stent is inserted into the longitudinal bore 84, the optional end cap is secured to the chamber 82 so that the end cap abuts one end of the stent 30, but does not force the stent against the flange 94 or ridge which is at the opposite end of the longitudinal bore from the end cap. Thus, after the end cap is secured to the chamber, the stent should have substantially no longitudinal movement within the longitudinal bore 84, and just have a slight amount of clearance between the diameter of the longitudinal bore and the outer diameter of the stent. The end cap will have a lumen or bore to allow the flow of electrolytic solution into the chamber.

Figure 9:
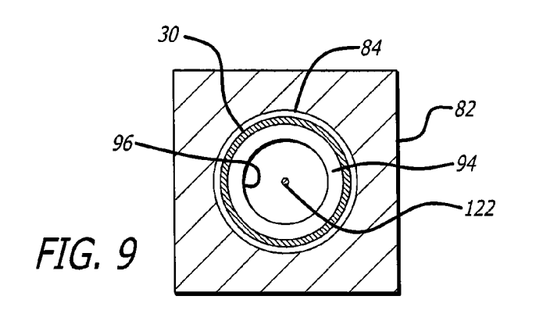
FIG. 9 is an end view of the assembly of FIG. 8.

With further reference to FIGS. 8 and 9, the stent 30 is positioned inside the longitudinal bore 84 so that an electrolytic solution 100 can flow over the stent and dissolve metal from the stent by a process known as electrolytic machining. Electrolytic machining involves the application of an electrical current to the workpiece, in this case the stent 30, while flowing an electrolytic solution over the stent surface. The stent acts as an anode and is dissolved into the electrolytic solution toward the cathode of the system. The rate at which metal is dissolved from the surface of the stent struts will vary depending on the velocity of the electrolyte at any surface location on the stent struts. This is due to the speed at which material can be swept away from the surface of the stent struts. In the embodiment shown in FIGS. 8 and 9, the stent is the anode (+) 120 and a wire 122 that extends through the longitudinal bore 84 is a cathode 124. A power source 126 provides a current that flows from the anode 120, thereby polarizing the anode, and encouraging metal ions on the surface of the stent to diffuse through the electrolytic solution 100 toward the cathode 122. The composition of the electrolytic solution 100 is well known in the art and can vary depending upon the type of metal used to form the stent. The current density is greatest at the high points on the inner surface of the stent and lowest at lower points on the stent which are the outer surface of the stent. The rate of the electrochemical reaction is directly proportional to the density and the flow rate of the electrolytic solution so that increased current density at the raised points causes the anodic metal to dissolve faster at these points as metal dissolves from the surface of the stent. Further factors that affect the rate at which metal is removed from the stent struts are the current density, the duration of the applied current, the flow rate of the electrolytic solution 100, and the temperature of the electrolytic solution.

The wire 122 forming the cathode 124 can typically be formed of numerous configurations such as 90% platinum and 10% iridium clad over a niobium core. Other types of wires for use as cathodes are well known in the art.

One of the factors that determines the amount of metal and the rate of removal of metal from the stent struts is the flow rate of the electrolytic solution 100. In one embodiment, the flow rate of the electrolytic solution 100 is in the range of 0.2 mL per second to 50.0 mL per second. These flow rates are by way of example only, and can be varied depending upon numerous factors including the type of metal from which the stent is formed, the size of the stent, and the transverse cross-sectional shapes of the stent struts. The pump used to pump the electrolytic solution through the chamber 82 is not shown, and is well known in the art.

In further keeping with the invention, and referring to FIGS. 10A-10D, an electrolytic solution 100 flows over the stent struts 102 of stent 30. The electrolytic solution 100 enters the chamber 82 (through a lumen or bore in the end cap) and flows through the longitudinal bore 84 of the chamber. As can be seen in FIGS. 10A-10D, as the electrolytic solution flows over the stent struts 102, which typically have a rectangular cross-section as shown in FIG. 7, the first edge 106 of the stent strut becomes rounded and metal is removed from the first edge at a greater rate than at the second edge 108. In other words, the first edge 106 of the stent strut 102 is directly in the flow of the electrolytic solution 100 and metal will dissolve from the first edge at a rate faster than metal being dissolved from the second edge 108 on the downstream side of the electrolytic solution. As the electrolytic solution 100 travels over the stent strut 102, it dissolves less metal from second edge 108 since that edge is not directly in line with the flow of electrolytic solution. Thus, the second edge 108 will have a thickness that is greater than the thickness of first edge 106, and both the first edge and the second edge will be curved, thereby taking the shape of an airfoil or hydrofoil. It is noted that first edge 106 does not have so much metal removed that it resembles a knife edge, like a typical airfoil or hydrofoil, but some metal is removed so that the first edge 106 has less thickness than the second edge 108, yet the stent strut 102 still has enough cross-sectional area so as to not compromise the structural integrity of the stent. In other words, after processing with the electrolytic solution 100, the stent 30 still will have the structural integrity to hold open a vessel, such as a coronary artery, yet will have the benefit of the stent struts having an airfoil shaped cross-section in order to reduce turbulent blood flow.

More specifically, the strut radial thickness of stent 30 for a coronary artery stent typically is about 0.0032 inch. It will be appreciated, however, that the strut radial thickness can be thicker or thinner, depending on the stent design and where it is implanted. Thus, the strut radial thickness can be in the range from 0.060 inch to 0.002 inch. The present invention reduction in radial thickness of the struts can range from about 5% to about 20% at the first edge 106 and from about 3% to about 15% at the second edge 108. Preferably, the radial thickness of the first edge 106 is reduced by 20% and radial thickness of the second edge is reduced by 5%. As an example, for a stent strut that has a radial thickness of 0.0032 inch, the first edge 106 will be 20% thinner, or about 0.0026 inch and the second edge 108 will be 5% thinner, or about 0.003 inch. Further, the strut surface extending between the first edge 106 and second edge 108 may be straight or slightly curved and essentially form a taper, gradually getting thicker going from the first edge toward the second edge.

Referring to FIGS. 8-10D, it will be appreciated that those stent struts 102 that will benefit the most from the use of the electrolytic solution 100 in chamber 82 are those stent struts that are perpendicular to the flow of the electrolytic solution. Thus, for example, referring to FIG. 6, peak 69 and straight portions 58 are stent struts that are substantially perpendicular to the longitudinal axis of the stent and thus are perpendicular to the flow of the electrolytic solution 100. It is expected that these stent struts will have a cross-sectional shape that resembles an airfoil or hydrofoil as previously discussed. Those stent struts that are not substantially perpendicular to the direction of the flow of the electrolytic solution 100, also benefit from the present invention in that the transverse cross-section may not have a perfect airfoil-shaped cross-section, however, the first edge 106 of such stent struts will generally have more metal removed than the second edge 108 of such stent struts.

The stent 30 of the present invention can be mounted on a balloon catheter similar to that shown in FIG. 1. The stent is tightly compressed or crimped onto the balloon portion of the catheter and remains tightly crimped onto the balloon during delivery through the patient's vascular system. When the balloon is expanded, the stent expands radially outwardly into contact with the body lumen, for example, a coronary artery. When the balloon portion of the catheter is deflated, the catheter system is withdrawn from the patient and the stent remains implanted in the artery. Similarly, if the stent of the present invention is made from a self-expanding metal alloy, such as nickel-titanium or the like, the stent may be compressed or crimped onto a catheter and a sheath (not shown) is placed over the stent to hold it in place until the stent is ready to be implanted in the patient. Such sheaths are well known in the art. Further, such a self-expanding stent may be compressed or crimped to a delivery diameter and placed within a catheter. Once the stent has been positioned within the artery, it is pushed out of the catheter or the catheter is withdrawn proximally and the stent held in place until it exits the catheter and self-expands into contact with the wall of the artery. Balloon catheters and catheters for delivering self-expanding stents are well known in the art.

Figure 10A:
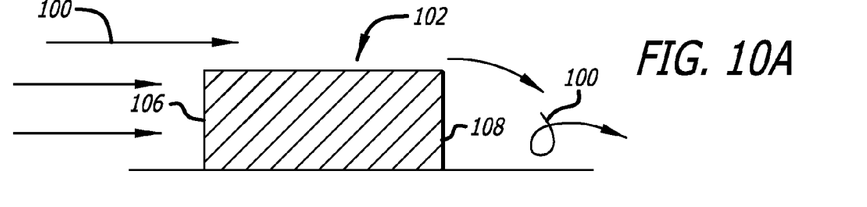
FIGS. 10A-10D are a series of cross-sectional views of a single strut of the stent of the invention as electrolytic solution passes over the stent and progressively removes metal from the stent strut.
Figure 10B:
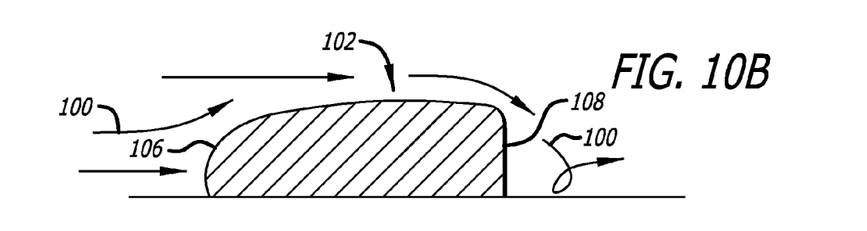
Figure 10C:
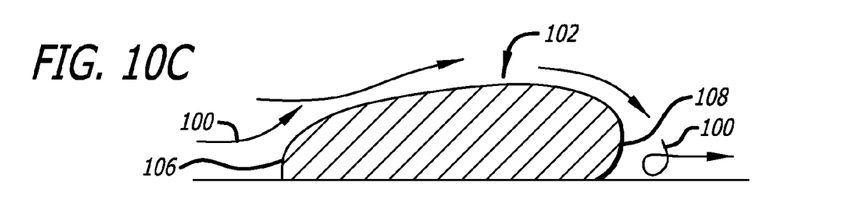
Figure 10D:
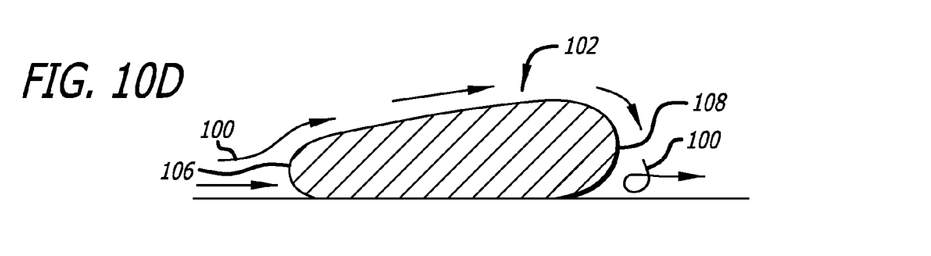
Figure 11:
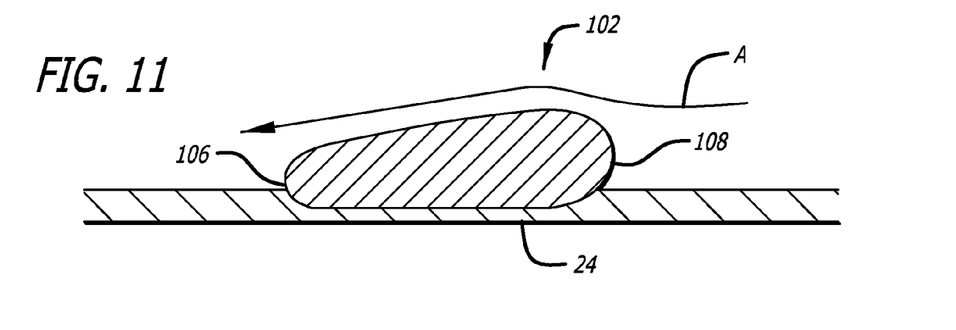
FIG. 11 is a transverse cross-sectional view of an airfoil-shaped stent strut partially imbedded in an artery wall.

It is important to note that the airfoil shape of the stent strut 102 as shown for example in FIG. 10D, has a second edge 108 that is thicker than a first edge 106. When the stent 30 is implanted in a vessel, such as a coronary artery 24 shown in FIG. 11, it is more likely that blood in the artery will flow from the second edge 108 toward the first edge 106 much like the airflow over the airfoil of an airplane wing. In other words, the leading edge (second edge 108) of the stent strut 102 is thicker than the trailing edge (first edge 106), and as blood flows along the strut surface as shown by arrow A, it maintains a laminer flow without disturbing the adjacent vasculature as much as if the stent strut were more rectangular-shaped. Further, the present invention using electrolytic machining may also form a stent strut that has a tapered shape rather than an airfoil shape, and still be beneficial in the reduction of blood flow turbulence.

Electrolytic machining processing can be performed by companies such as Kennemetal Extrude Hone, Grand Rapids, Mich.

While the invention has been illustrated and described herein, in terms of its use as an intravascular stent, it will be apparent to those skilled in the art that the stent can be used in other body lumens. Other modifications and improvements may be made without departing from the scope of the invention.

What is claimed:

1. A method for removing metal from a stent, comprising:
providing a chamber having a longitudinal bore extending therethrough;
inserting a stent in the chamber;
attaching an end cap to one end of the chamber so that the end cap abuts the stent and moves the stent into contact with a flange in the longitudinal bore;
attaching a power source to the chamber to form an anode;
placing a cathode within an inner lumen of the stent;
pumping an electrolytic solution through a lumen in the end cap and through the longitudinal bore and through the inner lumen of the stent to electrochemically remove portions of the inner lumen of the stent wherein the electrolytic solution has a flow rate in the range of 0.2 mL per second to 50.0 mL per second; and
wherein removal of metal from the stent struts results in a transverse cross-section in the shape of an airfoil.

2. The method of claim 1, wherein the cathode is a wire extending through the inner lumen of the stent.

3. The method of claim 1, wherein only metal is removed from an inner surface of the stent.

4. The method of claim 3, wherein metal is removed from stent struts extending transverse to a longitudinal axis of the stent.

* * * * *